United States Patent [19]

Waldon

[11] 4,250,833
[45] Feb. 17, 1981

[54] ENTOMOLOGICAL APPARATUS

[76] Inventor: Katsuhiko Waldon, 4000 Shady Oaks Dr., Ooltewah, Tenn. 37363

[21] Appl. No.: 43,631

[22] Filed: May 30, 1979

[51] Int. Cl.³ ............................................. A01K 67/00
[52] U.S. Cl. ........................................ 119/1; 119/15
[58] Field of Search ................ 119/1, 5, 15; 220/4 B; 215/6, 12 R; 47/69

[56] References Cited

U.S. PATENT DOCUMENTS

| | | | |
|---|---|---|---|
| 948,805 | 2/1910 | Akerlind | 119/1 |
| 2,151,589 | 3/1939 | Falls | 119/1 |
| 2,174,305 | 9/1939 | Austin | 119/1 |
| 3,687,110 | 8/1972 | Braunhut | 119/15 X |
| 3,903,642 | 9/1975 | Yellin | 47/69 |
| 4,117,805 | 10/1978 | Ward | 119/5 |

Primary Examiner—Hugh R. Chamblee
Attorney, Agent, or Firm—Lamont Johnston

[57] ABSTRACT

An entomological apparatus is provided to facilitate the observation and study of insects, e.g. ants. The apparatus is comprised of a first substantially transparent enclosure having inner and outer surfaces. Preferably this transparent enclosure is a sphere. The apparatus is further comprised of a second enclosure, preferably a hemisphere including a planar wall. This second enclosure is within the first enclosure. The second enclosure has inner and outer surfaces. A portion of the outer surface of the second enclosure and a portion of the inner surface of the first enclosure form an environmental chamber for observing insects. In the preferred embodiment the environmental chamber is formed by maintaining the spherical first enclosure concentric with the hemispherical second enclosure. The apparatus is further comprised of an access means through the first enclosure for enabling placement of insects and environmental elements within the first enclosure.

1 Claim, 4 Drawing Figures

U.S. Patent  Feb. 17, 1981  Sheet 1 of 2  4,250,833

ENTOMOLOGICAL APPARATUS

BACKGROUND OF THE INVENTION

1. Field of the Invention

This invention relates to Entomological apparatuses, more particularly to an apparatus for permitting the observation and study of insects, especially insects of the hymenopterous order, i.e. wasps, bees, ants, etc. Insects of these species usually exhibit some degree of social organization and consequently live in communities or colonies making them susceptible for group observation and study of their behavior patterns.

The entomological apparatus of this invention is suitable for research and scientific experiments, as well as educational purposes for children and adults.

2. Prior Art

Entomological apparatuses are known in the art, see for example the following U.S. Pat. Nos.:

2,080,160 to Austin;
3,088,134 to Abel; and
3,653,357 to Sheidlower et al.

Generally, these known apparatuses are rectangular enclosures having a shallow chamber between two transparent surfaces with various surfaces for the insects contained therein to crawl upon for observation. In this chamber are placed environmental elements necessary for the insects growth and maintenance.

These known apparatuses suffer in that they are not decorative and they are complicated in structure and difficult to assemble and manufacture.

SUMMARY OF THE INVENTION

It is an object of this invention to provide an entomological apparatus to facilitate the observation and study of insects, the apparatus being of the general character described herein and having the aforementioned advantageous design and construction characteristics.

Specifically, it is an object of the present invention to provide an entomological apparatus which permits insects to thrive in a natural environment and allow the full and complete observation of such insects.

Another object of this invention is to provide an apparatus which is simple to manufacture and easy to assemble.

Another object of this invention is to provide an entomological apparatus which is unique in design and decorative, and yet provides for the observation of the insects contained therein.

The present invention is an entomological apparatus to facilitate the observation and study of insects. The apparatus is comprised of:

(a) a first substantially transparent enclosure having inner and outer surfaces;
(b) a second enclosure within the first enclosure, the second enclosure having inner and outer surfaces, wherein a portion of the outer surface of the second enclosure and a portion of the inner surface of the first enclosure form an environmental chamber for observing insects; and
(c) an access means through the first enclosure for enabling placement of insects and environmental elements therein.

The above and other objects, features and advantages of this invention will become apparent from the following description of the preferred embodiment in connection with the accompanying drawings.

DETAILED DESCRIPTION OF THE INVENTION

FIGS. 1 through 4 depict a specific preferred embodiment of the entomological apparatus of this invention, generally designated (10). The apparatus (10) is used to facilitate the observation and study of insects. It is generally preferred that the insects be of the hymenopterous order for optimum pleasure in viewing.

Figure 1:
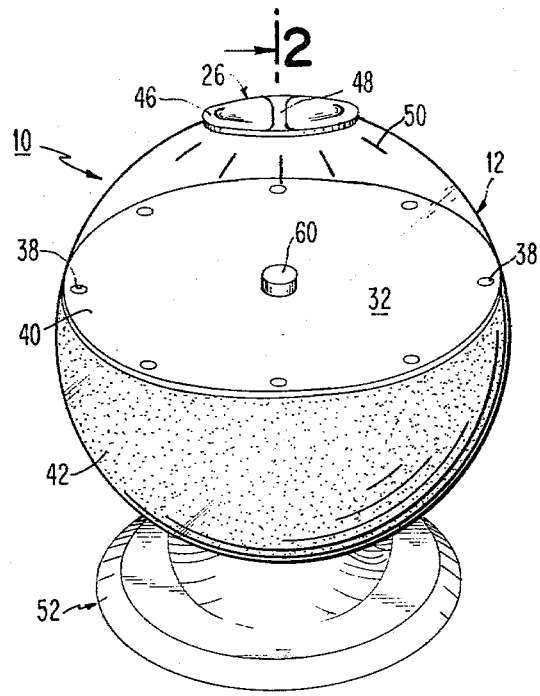
FIG. 1 is a perspective view of an embodiment of the entomological apparatus of this invention.
Figure 2:
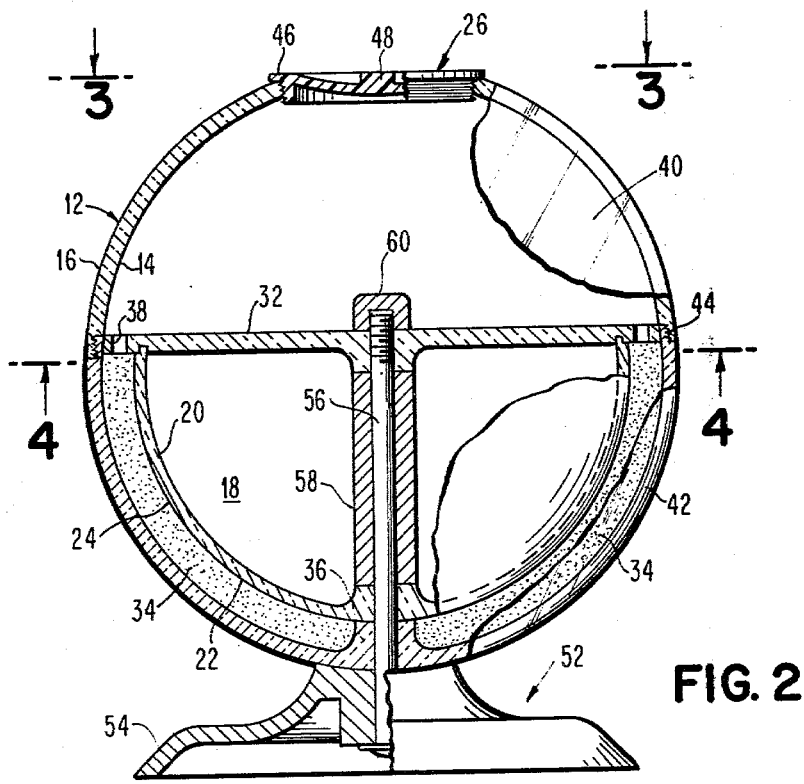
FIG. 2 is a sectional view of the entomological apparatus of FIG. 1 taken along line 2—2 of FIG. 1.
Figure 3:
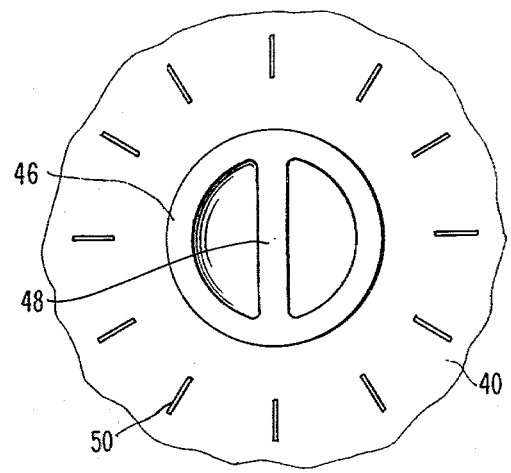
FIG. 3 is a partial view of the entomological apparatus of FIG. 1 taken along line 3—3 of FIG. 2.
Figure 4:
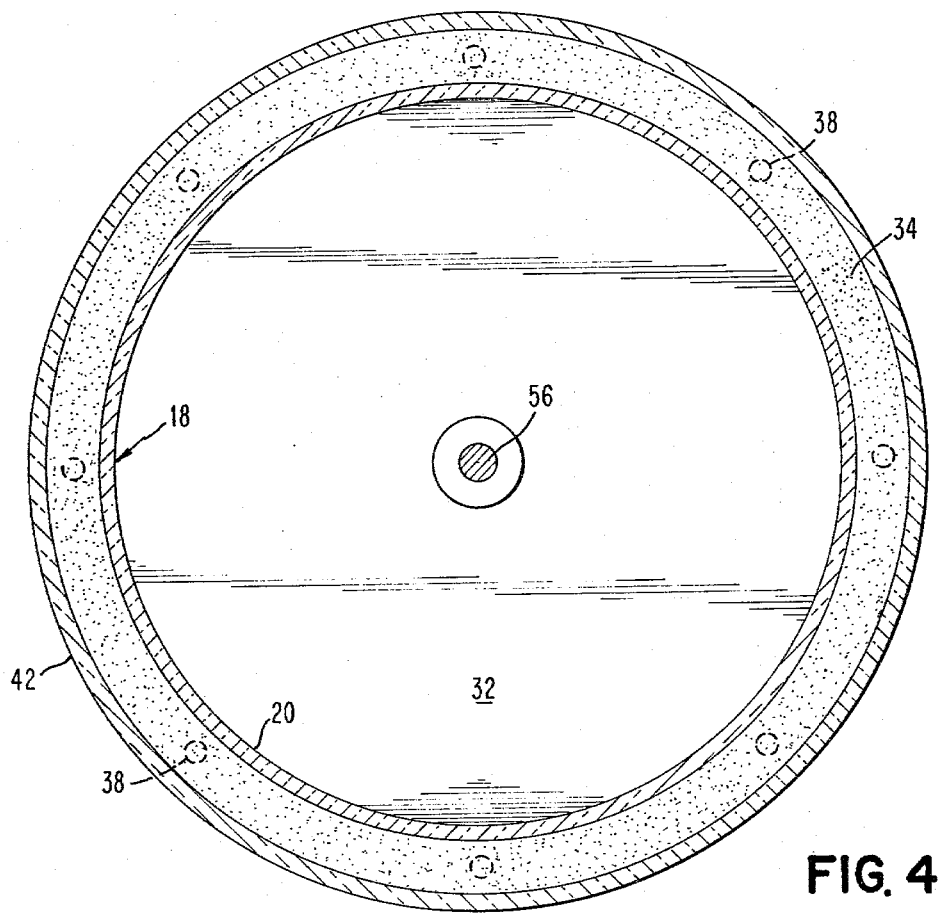
FIG. 4 is a sectional view of the entomological apparatus of FIG. 1 taken along line 4—4 of FIG. 2.

Referring to FIG. 2, the apparatus (10) of this invention is comprised of a first substantially transparent enclosure (12) having an inner surface (14) and an outer surface (16). The apparatus (10) is further comprised of a second enclosure, generally depicted as (18). The second enclosure (18) is located within the first enclosure (12). The second enclosure (18) has an inner surface (20) and an outer surface (22). A portion of the outer surface (22) of the second enclosure (18) and a portion of the inner surface (14) of the first enclosure (12) form an environmental chamber, generally designated (24), for observing insects.

An access means, generally designated (26) passes through the first enclosure (12) enabling placement of insects and environmental elements, such as food, sand, water, etc. therein.

Preferably, for decorative appearance and easy observation and manufacture, the second enclosure (18), is also transparent. Alternatively, however, only the first enclosure (12) may be transparent for this is the surface through which the primary observation of the insects occurs.

Enclosures (12 & 18) of this invention may be of any shape, rectangular, oval, etc. keeping with the objects of this invention. It is highly preferred, however, that the first enclosure (12) be a sphere and the second enclosure (18) be a hemisphere. This is clearly shown in the preferred embodiment of FIGS. 1 through 4. The hemisphere includes a planar wall (32). In this preferred embodiment the first enclosure (12) and the second enclosure (18) are maintained substantially concentric with each other to form the environmental chamber (24). The environmental chamber (24) is preferably formed in the lower half (42) of the first enclosure (12). This is to allow settling of the sand (34) within the environmental chamber.

The first enclosure (12) and the second enclosure (18) are maintained concentric with each other by a plurality of spacers between the inner surface (14) of the first enclosure (12) and the other surface (22) of the second enclosure (18).

Referring to FIG. 2, the planar wall (32) extends to the inner surface (14) of the first enclosure (12). This extension closes off the environmental chamber (24) and assists in maintaining the first and second enclosures (12 & 18) concentric with each other. Additionally, in the preferred embodiment a center spacer (36) assists in supporting and maintaining the second enclosure (18) concentric with the first enclosure (12).

Preferably, the extension of the planar wall (32) has insect access holes (38) passing from the upper half (40) of the first enclosure (12) through the planar wall (32) to the environmental chamber (24) in the lower half (42) of the first enclosure (12). Preferably the insect access holes (38) are spaced every 45° around the periphery of the planar wall (32). The access holes (38) allow the insects which are in the environmental chamber (24) to have access to the upper half (40) of the first enclosure (12) and to walk about on the planar wall (32).

Preferably the upper half (40) and the lower half (42) of the first enclosure (12) are detachably mounted to each other. Preferably this may be accomplished by threads (44) around the peripheries of the upper and lower halves (40 & 42) of the first enclosure (12). It is desirable to provide such detachably mounted halves (40 & 42) for easy access to and assembly of the apparatus (10), replacement of environmental elements within the environmental chamber (24) and general ease of manufacture.

Preferably the access means (26) is a handhole through the upper half (40) of the first enclosure (12). The handhole has a detachably mounted handhole cover (46) attached thereto. Preferably the handhole cover (46) is threadably mounted to the handhole and has a holding means (48) attached thereto for threading and unthreading the handhole cover (46). The access means (26) allows for access to the upper half of the first enclosure (40) to permit insertion of insects and feed and other environmental elements for the care of the insects.

Additionally it is preferred that vent slots (50) be provided in the upper half (40) of the first enclosure (12) so that the insects can receive proper circulation of air. Preferably the vent slots (50) are located about the periphery of the first enclosure (12), preferably every 30°, or every 15°.

Preferably the entomological apparatus (10) has a support means, generally designated (52) for supporting the apparatus (10) so that the planar wall (32) is substantially horizontal. This support means (52) may be of any shape or form, including a suspension means to accomplish such object. A preferred support means (52) is depicted in FIG. 2. This preferred support means (52) consists of a base (54) which is attached to the outer surface (16) of the first enclosure (12). Preferably this is accomplished by a bolt (56) passing through the base (54), the first enclosure (12) and the second enclosure (18) and terminating at the planar wall (32). Preferably this bolt (56) is enclosed in an elongated member (58) which connects the inner surface (20) of the planar wall (32) with the diametrically opposite inner surface (20) of the second enclosure. The terminal point of the bolt (56) is covered with a protective cap (60). The foregoing arrangement allows for maintenance of the base (54) and the first and second enclosures (12 & 18) in a fixed relationship to each other, i.e. maintaining the concentricity of the enclosures (12 & 18).

In use, one assembles the entomological apparatus, as can be readily determined by one skilled in the art in view of FIGS. 1-4, and places insects within the first enclosure. The insects maintain their environment within the environmental chamber (24), and can be observed through the first enclosure. Their actions on the planar wall (32) may also be observed.

The entomological apparatus of this invention provides for a decorative, easily manufactured and assembled unit for observing insects.

The above cited embodiment is intended as exemplary; while it has been described with a specific implementation thereof, other modifications and changes may be made in the embodiment as set forth and will be apparent to those skilled in the art. It should therefore be understood that all material herein described or shown in the accompanying drawings is to be interpreted as illustrative and not in a limiting sense.

What is claimed is:

1. An entomological apparatus to facilitate the observation and study of insects comprising:
   (a) a substantially transparent spherical outer enclosure having inner and outer surfaces;
   (b) a substantially transparent hermispherical inner enclosure having a circular planar wall within the lower half of the first enclosure, the planar wall extending to the inner surface of the first enclosure, thereby maintaining the enclosures concentric with each other to form an environmental chamber between the enclosures and closing off the environmental chamber, the planar wall having insect access holes passing from the upper half of the outer enclosure through the planar wall to the environmental chamber;
   (c) access means through the outer enclosure for enabling placement of insects and environmental elements therein; and
   (d) means supporting the apparatus so that the planar wall is substantially horizontal including a base attached to the outer enclosure by a bolt passing through the base, the outer enclosure and the inner enclosure, thereby maintaining the base and the enclosures in fixed relationship to each other.

* * * * *